United States Patent [19]

Breglia

[11] Patent Number: 4,702,575
[45] Date of Patent: Oct. 27, 1987

[54] HELMET MOUNTED EYE TRACKER USING A POSITION SENSING DETECTOR

[75] Inventor: Denis R. Breglia, Altamonte Springs, Fla.

[73] Assignee: The United States of America as represented by the Secretary of the Navy, Washington, D.C.

[21] Appl. No.: 262,153

[22] Filed: May 11, 1981

[51] Int. Cl.$^4$ .............................................. A61B 3/14
[52] U.S. Cl. ................................................... 351/210
[58] Field of Search ..................... 351/7, 13, 16, 210, 351/211, 221

[56] References Cited

U.S. PATENT DOCUMENTS

| | | | |
|---|---|---|---|
| 3,236,578 | 2/1966 | Mackworth et al. | 351/7 |
| 3,450,466 | 6/1969 | Streisinger | 351/7 |
| 3,542,457 | 11/1970 | Balding et al. | 351/7 |
| 3,712,716 | 1/1973 | Cornsweet et al. | 351/210 |
| 4,034,401 | 7/1977 | Mann | 351/210 |
| 4,102,564 | 7/1978 | Michael | 351/7 |

*Primary Examiner*—Rodney B. Bovernick
*Attorney, Agent, or Firm*—Robert W. Adams

[57] ABSTRACT

A helmet mounted eye tracker is disclosed for monitoring the position of the cornea of a human eye which includes an infrared light source for projecting a pulsed infrared light beam along a first optical path, a mirror for redirecting the pulsed infrared light beam along a second optical path, and a beam splitter for redirecting the pulsed infrared light beam onto the cornea of the eye such that within the eye a virtual image is formed which changes position with movement of the cornea of the eye. The virtual image formed within the eye is then redirected along the second optical path by the beam splitter to the mirror which, in turn, redirects the virtual image to a collecting lens positioned along the first optical path. The collecting lens will then focus the virtual image upon the active area of an infrared light detector which will provide at its output square wave signals indicative of the X and Y coordinate positions of the cornea of the eye within the active area of the infrared light detector.

6 Claims, 2 Drawing Figures

HELMET MOUNTED EYE TRACKER USING A POSITION SENSING DETECTOR

BACKGROUND OF THE INVENTION

1. Field of the Invention

This invention relates generally to eye position movement. In particular, this invention relates to a helmet mounted eye tracker which monitors the eye position movement of the cornea of the human eye.

2. Description of the Prior Art

Heretofore, numerous oculometers and other eye-tracking apparatus have been employed to monitor the eye position movement of the human eye. Such systems of the prior art are too numerous to discuss herewith. Besides most thereof constitute prior art devices which are well known to the artisan, thereby obviating the need for further discussion thereof.

Of course, there are several prior art devices which are of some significance, inasmuch as they at least remotely or indirectly concern subject matter that is pertinent to the apparatus constituting the instant helmet mounted eye tracker using a position sensing detector.

For example, U.S. Pat. No. 3,462,604 to K. A. Mason discloses an oculometer for determining the orientation of an eyeball by measuring the position of the image of light reflected from the retina of the eye relative to the position of the image reflected from the front surface of the eye.

U.S. Pat. No. 3,473,868 discloses an eye measuring instrument employing a modulated invisible light source which illuminates the eye, and a pair of photocells directed to the interface of portions of the eye with different light reflecting properties. The interfaces selected move in response to eye movement or pupil area change, and the changes in the photocell outputs are a measure of the eye movement or pupil area change.

U.S. Pat. No. 4,145,122 to G. A. Rinard et al discloses an apparatus for monitoring the position of the eye, and for generating an electrical signal based upon the eye's displacement from a neutral position. The apparatus is characterized by a pair of eyeglasses modified to provide an infrared mirror on the inside surface of one lens, an infrared light emitting diode located on the nosepiece in position to produce a virtual image thereof within the wearer's eye as reflected from the infrared mirror, and an image detector mounted on the bow of the eyeglass adjacent the mirror filtered to respond only to infrared light and effective to locate the position within the eye of the reflected light emitting diode image.

Unfortunately, the aforementioned devices of the prior art ordinarily leave something to be desired, especially from the standpoints of position measurement accuracy and response time; that is, the aforementioned devices of the prior art do not allow for position measurement at high rates. In addition, the aforementioned devices of the prior art do not operate in exactly the same manner as the subject invention and contain a combination of elements that is somewhat different from that of the present invention.

SUMMARY OF THE INVENTION

The subject invention overcomes some of the disadvantages of the prior art, including those mentioned above, in that it comprises a relatively simple eye tracker for monitoring the movement of the cornea of the human eye.

Included in the subject invention is an infrared light source adapted for projecting a pulsed infrared light beam along a first optical path, a mirror for redirecting the pulsed infrared light beam along a second optical path, and a beam splitter which redirects the pulsed infrared light beam onto the cornea of the eye so as to form within the eye a virtual image that changes position upon movement of the cornea of the eye.

The virtual image formed within the eye is, in turn, redirected along the second optical path to the mirror which then redirects the aforementioned virtual image along the first optical path to a collecting lens. The collecting lens will focus the virtual image upon the active area of an infrared light detector which will, in turn, provide at the output thereof square wave signals indicative of the X and Y coordinate positions of the cornea of the eye within the active area of the infrared light detector.

DESCRIPTION OF THE PREFERRED EMBODIMENT

Figure 1:
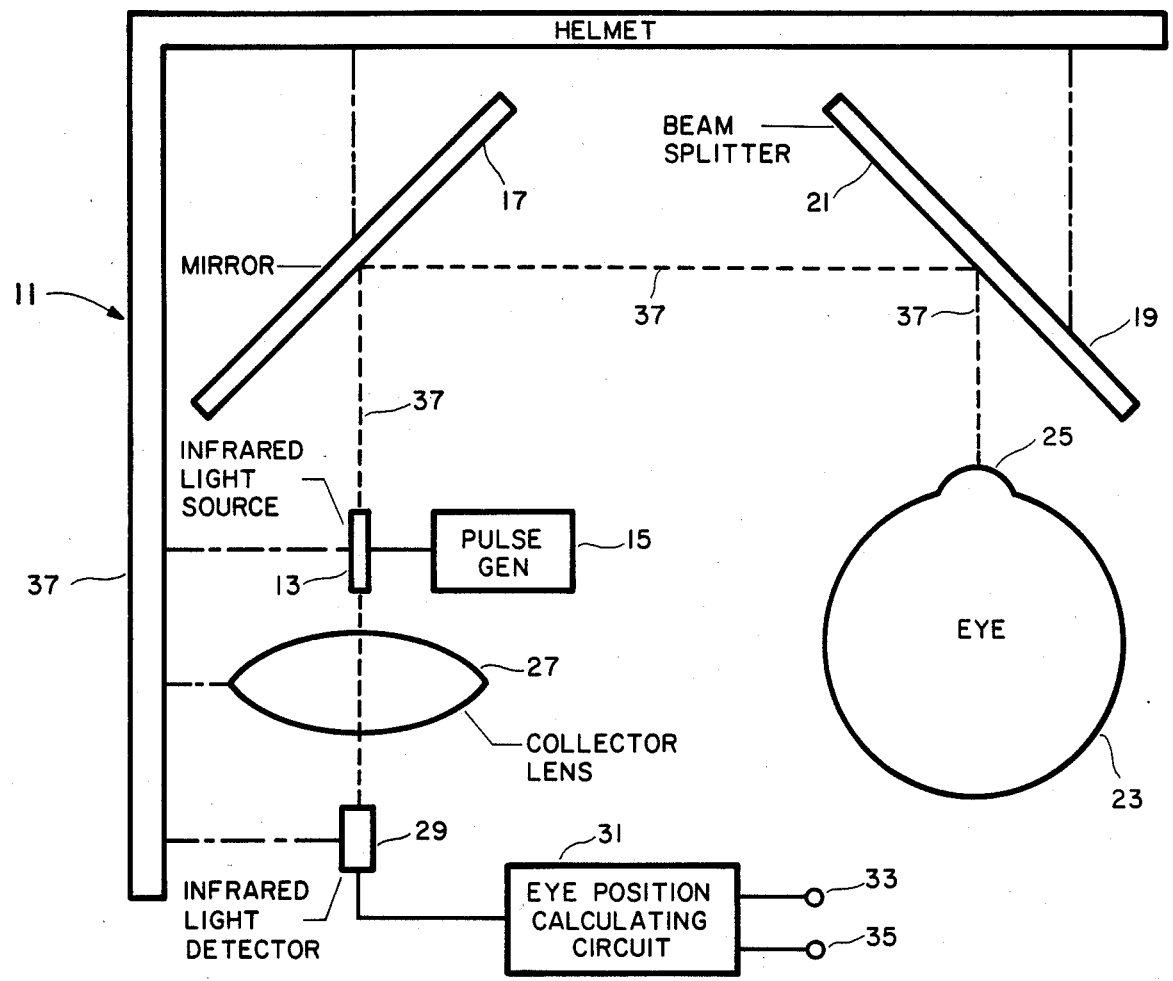
FIG. 1 illustrates in optical schematic and block diagram form the system constituting the subject invention.

The preferred embodiment of the subject invention will now be discussed in some detail in conjunction with all of the figures of the drawing, wherein like parts are designated by like reference numerals, insofar as it is possible and practical to do so.

Referring now to FIG. 1, there is shown a helmet mounted eye tracker 11 which includes therein an infrared light source 13, the input of which is connected to the output of a pulse generator 15. Infrared light source 13, in turn, comprises an infrared light emitting diode of conventional design, the particular one shown being a five milliwatt gallium arsenide light emitting diode having a 10° emission cone.

Along a first optical path and downstream from infrared light source 13 is an aluminized glass mirror 17, the reflective surface of which is positioned at 45° with respect to the aforementioned first optical path. Moreover, the reflective surface of mirror 17 makes an angle of 45° with a second optical path such that the angle between the first and second optical paths is 90°.

Positioned downstream from mirror 17 along the aforesaid second optical path is a beam splitter 19. Beam splitter 19, in turn, has an infrared light reflective surface 21, with the angle of the plane thereof being such that it makes a 45° angle with respect to the axis of the aforesaid second optical path and thus forms a third optical path as a result of the reflection of infrared light therefrom which, in turn, makes a 90° angle with the aforementioned second optical path. In addition, it should be noted at this time that beam splitter 19 is essentially transparent to all visible light within the spectral range of the human eye and, therefore, there is essentially no impairment of the user's normal vision when viewing an object positioned upstream from beam splitter 19 along the aforesaid third optical path.

Positioned downstream from beam splitter 19 along the aforesaid third optical path is an eye 23 of an observer having a cornea 25. The subject invention, as will be discussed more fully below, functions to measure the movement of cornea 25 of human eye 23 and provide analog signals indicative of such movement.

Spatially disposed upstream from infrared light source 13 along the aforesaid first optical path is a collector lens 27. Collector lens 27, in turn, is positioned approximately 150 millimeters from cornea 25 of human eye 23, has a diameter of twenty-five millimeters, and a focal length of seventy-five millimeters, thereby forming a unity magnification imaging system.

Spatially disposed upstream from collector lens 27 along the aforesaid first optical path is infrared light detector 29, which measures the movement of cornea 23 of human eye 25. Infrared light detector 29 is positioned approximately 150 millimeters from collector lens 27 such that collector lens 27 provides a unity magnification factor when directing an image to infrared light detector 29.

The output of infrared light detector 29 is connected to the input of an eye position calculating circuit 31, the first output of which is connected to an X coordinate output terminal 33, and the second output of which is connected to a Y coordinate output terminal 35.

Although any conventional infrared light detector that is compatible with the subject invention may be utilized therein, it has been found that a Model PIN SC/10D dual axis infrared light detector manufactured by United Detector Technology, of Culver City, Calif., performs quite well for such purpose. In addition, eye position calculating circuit 31 may be of the type described in U.S. Pat. No. 4,387,974, entitled Circuit for Calculating the Position of the Eye, by Albert H. Marshall and Gary M. Bond.

All of the aforementioned elements, excluding eye position calculating circuit 31, are connected to a conventionally designed helmet 37 by an appropriate attachment means, as respectively represented by the dashed lines therebetween.

The operation of the subject invention will now be discussed in conjunction with all of the figures of the drawing.

Referring now to FIG. 1, infrared light source 13 projects along the aforementioned first optical path a pulsed infrared light beam 37 having a frequency of ninety-six hertz. Infrared light source 13, in turn, is energized by pulse generator 15, which provides at the output thereof a pulsed signal having a frequency of ninety-six hertz so as to allow infrared light source 13 to project pulsed infrared light beam 37 along the aforesaid first, second, and third optical paths to human eye 23.

Figure 2:
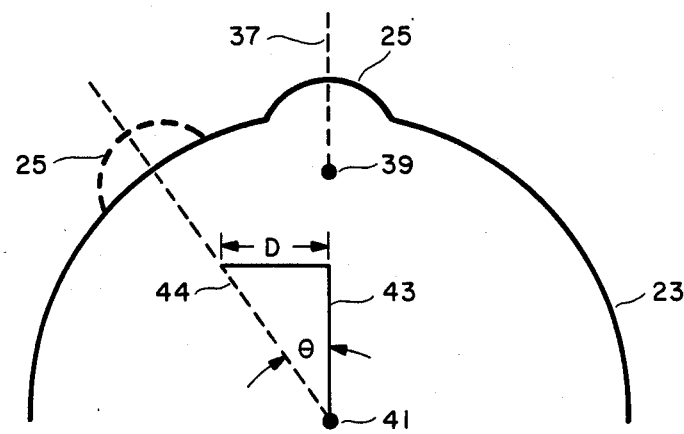
FIG. 2 is a diagram of the cornea of the eye when a pulsed infrared light beam is incident thereon.

Next, with reference to FIGS. 1 and 2, it can be seen that eye 23 is illuminated by infrared light source 13 in the manner described above. More specifically, infrared light beam 37 is reflected by the surface of cornea 25 of eye 23 and a virtual image 39 thereof is formed approximately four millimeters behind the surface of cornea 25.

The reflective characteristics of cornea 25 are such that cornea 25 has an effective radius of curvature of eight millimeters, and a reflectance of approximately two percent. This, in turn, causes virtual image 39 to be formed approximately four millimeters behind cornea 25 and in line with the direction of incident illumination. When eye 23 rotates, its center of rotation, designated by reference numeral 41, is a distance of 13.5 millimeters behind cornea 25 of eye 23. Therefore, virtual image 39 will displace with eye rotation in accordance with the relationship $$D = 5.5 \sin \theta, \quad (1)$$

where D is the displacement in millimeters from a line perpendicular to a predetermined reference line of sight 43 of eye 23, and $\theta$ is the angle of rotation from reference line of sight 43 to a line of sight 44 to which cornea 25 has been displaced from reference line of sight 43 because of eye movement.

It should be noted at this time that relationship one assumes that eye rotation is limited to an angular displacement of $\pm 45°$ from reference line 43. This, in turn, limits the displacement D in accordance with relationship one to $\pm 4$ millimeters from reference line 43. Accordingly, since collector lens 27 provides a unity magnification factor, as discussed above, infrared light detector 29 must have an active area or field of view of at least eight millimeters in diameter.

Virtual image 39 from human eye 23 is then directed along the aforesaid third optical path to beam splitter 19, which then redirects virtual image 39 along the aforesaid second optical path to mirror 17. Mirror 17, in turn, redirects virtual image 39 to collecting lens 27, which will then focus virtual image 39 onto the field of view of infrared light detector 29.

Infrared light detector 29 will provide at the output thereof a plurality of square wave signals indicative of the X and Y coordinate positions of cornea 25 of eye 23 within the field of view of infrared light detector 29. Each of the aforementioned square wave signals, in turn, has a frequency of ninety-six hertz.

Eye position calculating circuit 31 will, in response to the aforementioned square wave signals, calculate the X and Y coordinate positions of cornea 25 of eye 23 within the field of view of infrared light detector 29. Eye position calculating circuit 31 will then provide at terminal 33 a first analog signal indicative of the X coordinate position of cornea 25 within the field of view of infrared light detector 29, and a second analog signal indicative of the Y coordinate position of cornea 25 within the field of view of infrared light detector 29. For a complete description of the operation of eye position calculating circuit 29, reference is again made to U.S. Pat. No. 4,387,974, entitled Circuit for Calculating the Position of the Eye, by Albert H. Marshall and Gary M. Bond.

From the foregoing description, it may readily be seen that the subject invention comprises a new, unique, and exceedingly useful eye tracker for monitoring the position of the human eye which constitutes a considerable improvement over the known prior art. Obviously many modifications and variations of the present invention are possible in light of the above teachings. It is, therefore, to be understood that within the scope of the appended claims, the invention may be practiced otherwise than as specifically described.

What is claimed is:

1. An eye tracker for monitoring movement of an eye's cornea comprising, in combination:
    source means having an output adapted for projecting a pulsed infrared light beam having a predetermined frequency along a first predetermined light path;
    reflecting means spatially disposed downstream from said source means along said first light path adapted for redirecting said pulsed infrared light beam along a second predetermined light path, and for receiving and redirecting along said first light path a virtual image formed within said eye;

infrared beam splitting means spatially disposed downstream from said reflecting means along said second light path adapted for redirecting said pulsed infrared light beam onto the cornea of said eye that is positioned along a third predetermined light path so as to form said virtual image that changes position upon movement of the cornea of said eye, for receiving the virtual image formed within said eye, and for redirecting the virtual image formed within said eye along said second light path;

infrared sensing means positioned upstream from said source means along said first optical path, and having a field of view and an output adapted for receiving the virtual image formed within said eye, and for providing at the output thereof a plurality of square wave signals indicative of the X and Y coordinate positions of the cornea of said eye within the field of view of said sensing means; and collecting lens means positioned between said source means and said sensing means along said first light path adapted for focusing the virtual image formed within said eye upon the field of view of said sensing means.

2. The eye tracker of claim 1, wherein the frequency of said pulsed infrared light beam is ninety-six hertz.

3. The eye tracker of claim 1, wherein said sensing means comprises a dual axis infrared light detector.

4. The eye tracker of claim 1, further characterized by a pulse generator having an output connected to the input of said source means for providing a pulsed signal so as to effect the energization of said source means.

5. The eye tracker of claim 1, further characterized by an eye position calculating circuit having an input connected to the output of said sensing means for calculating, in response to said square wave signals, the X and Y coordinate positions of the cornea of said eye within the field of view of said sensing means.

6. The eye tracker of claim 1, further characterized by a helmet connected to each of the elements thereof for the mounting and supporting thereof in predetermined relative dispositions respectively.

* * * * *